US00PP28015P3

(12) United States Plant Patent
Albokari

(10) Patent No.: US PP28,015 P3
(45) Date of Patent: May 16, 2017

(54) SHRUB ROSE PLANT NAMED 'KASCT491-1'

(50) Latin Name: *Rosa damascena*
Varietal Denomination: KASCT491-1

(71) Applicant: Majed Albokari, Riyadh (SA)

(72) Inventor: Majed Albokari, Riyadh (SA)

(73) Assignee: Atomic Energy Research Institute (SA)

( * ) Notice: Subject to any disclaimer, the term of this patent is extended or adjusted under 35 U.S.C. 154(b) by 126 days.

(21) Appl. No.: 14/545,465

(22) Filed: May 7, 2015

(65) Prior Publication Data

US 2016/0330884 P1 Nov. 10, 2016

(51) Int. Cl.
*A01H 5/02* (2006.01)

(52) U.S. Cl.
USPC ..... Plt./107

(58) Field of Classification Search
USPC ..... Plt./101, 102, 107
See application file for complete search history.

(56) References Cited

PUBLICATIONS

Datta, S.K. 1997. Mutation studies on garden roses: A review. Proc Indian natan. Scil. Acad. B63, No. 1 & 2: 107-126.*
Peter Beales Roses. https://www.classicroses.co.uk/roses/rosa-damascena-shrub-rose.html. 1 page.*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Rosa damascena* named 'KASCT491-1' is disclosed, characterized by light pink flowers of a larger size than typical. Plants are compact, floriferous and begin flowering early in the season. The new cultivar is a *Rosa* typically suited for ornamental container and landscape use.

3 Drawing Sheets

Latin name of the genus and species: *Rosa damascena.*
Variety denomination: 'KASCT491-1'.

BACKGROUND OF THE INVENTION

The present invention constitutes a new and distinct variety of *Rosa damascena* which originated from a breeding program employing mutation induction technology coupled with tissue culture technology. Research and first propagation were carried out at a research greenhouse and trial station in Riyadh, Saudi Arabia.

Unpatented, proprietary mother plants of *Rosa damascena* were collected Oct. 2, 2011. Explants of the same were successfully initiated, established and proliferated in vitro using tissue culture technology. The cultures were irradiated with 5 different doses of gamma rays (10Gy, 20Gy, 30Gy, 40Gy, 50Gy, 70Gy) in mid 2012, and a total of over 5000 putative mutants were obtained in the M1V3 generation. The rooted population was grown to adult plants and then established in the field for evaluations.

The mutant 'KACST491-1' was selected as a single plant on 25 Apr. 2014 from the population of 5000 putative mutants established in the field at Riyadh, Saudi Arabia. The new mutant variety 'KACST491-1' can be distinguished from its non-irradiated parent primarily from its flower coloration and growth habit. Tissue culture as well as asexual reproduction by cuttings of 'KACST491-1' was carried out in mid 2014 at a research laboratory in Riyadh, Saudi Arabia. The initial and other subsequent propagations have demonstrated that the characteristics of 'KACST491-1' are true to type and are transmitted from one generation to the next.

SUMMARY OF THE INVENTION

The cultivar 'KASCT491-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KASCT491-1'. These characteristics in combination distinguish 'KASCT491-1' as a new and distinct *Rosa damascena* cultivar:

1. Light pink flowers.
2. Compact plant habit.
3. Larger flower size than known *Rosa damascena*, due to higher petal count.
4. Early season onset of flowering.
5. Prolific flowering.

PARENTAL COMPARISON

The new variety differs from the parent variety in flower color, petal count and plant height. Table 1 specifies these differences.

TABLE 1

| No. | Characteristic | 'KACST491-1' | Non-irradiated control |
|---|---|---|---|
| 1. | General flower color | Light pink | Purplish red |
| 2. | Average number of petals | 44 | 30 |
| 3. | Average flower diameter | 9 cms | 6 cms |

TABLE 1-continued

| No. | Characteristic | 'KACST491-1' | Non-irradiated control |
|---|---|---|---|
| 4. | Average height of plant | 90 cms | 147 cms |
| 5. | Average days to flower after field establishment | 26 | 120.8 |

COMMERCIAL COMPARISON

Plants of the new cultivar 'KASCT491-1' are similar to the commercial variety *Rosa damascena* 'Celsiana', unpatented, in most horticultural characteristics. 'However, the new variety differs from 'Celsiana' in the following:

1. Maximum height of 'KACST491-1' is about 90 cms as compared to 185 cms of 'Celsiana'.
2. Flower color of 'KACST491-1' is light pink as compared to soft, whitish pink of 'Celsiana'.
3. Average flower diameter of 'KACST491-1' is 9.0 cms as compared to 6.5 to 7.0 cms of 'Celsiana'.
4. Average number of petals for 'KACST491-1' is 44 as compared to approximately 16 for 'Celsiana'.

Plants of the new cultivar 'KASCT491-1' are similar to the commercial variety *Rosa damascena sempflorens* 'York and Lancaster', unpatented, in most horticultural characteristics. 'However, the new variety differs from 'York and Lancaster' in the following:

1. Maximum height of 'KACST491-1' is about 90 cms as compared to 215 cms of 'York and Lancaster'.
2. Flower color of 'KACST491-1' is light pink as compared to half white and half pink of 'York and Lancaster'.
3. Average diameter of flower of 'KACST491-1' is 9.0 cms as compared to 6.5 cms of 'York and Lancaster'.
4. Average number of petals for 'KACST491-1' is 44 as compared to around 30 for 'York and Lancaster'.

BRIEF DESCRIPTION OF THE PHOTOGRAPHS

The accompanying color photographs illustrate the typical characteristics of the stem, leaves and flowers of 'KACST491-1'. Additionally, the color difference between the flower of the non-irradiated parent variety and the flower of 'KACST491-1' is illustrated.

Figure 1:
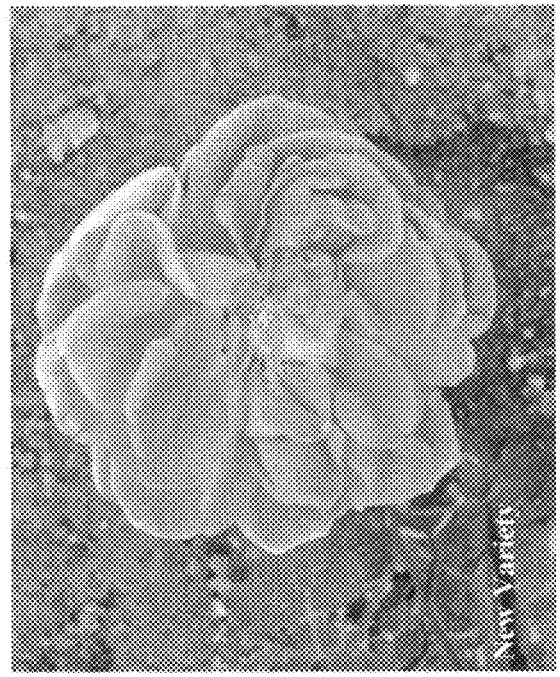
FIG. 1 Illustrates a flower of the parent variety on the left of the photo, flower of 'KACST491-1' to the right of the photo.
Figure 1:
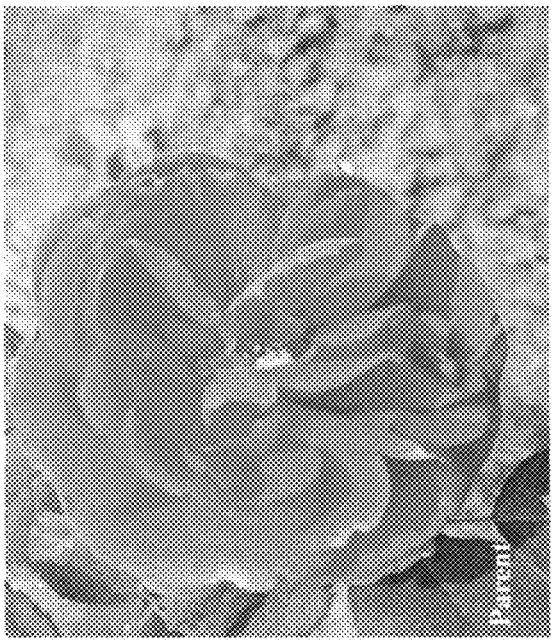
Figure 2:
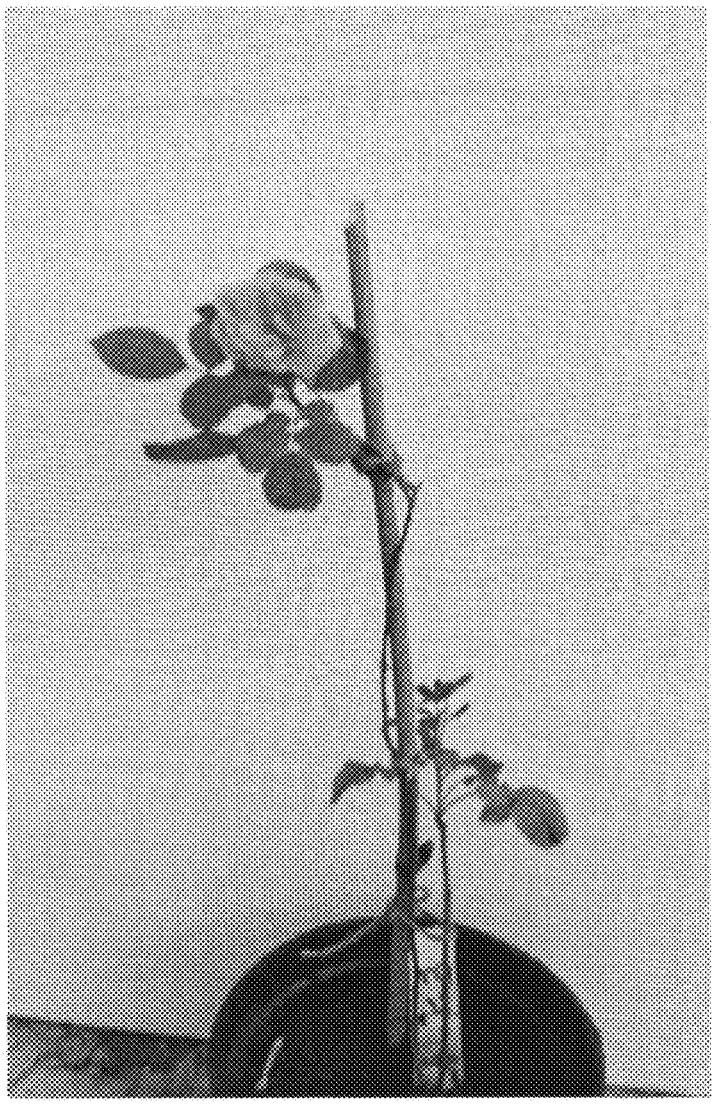
FIG. 2 illustrates a young flowering plant of 'KACST491-1' grown in a greenhouse in Riyadh, Saudi Arabia.
Figure 3:
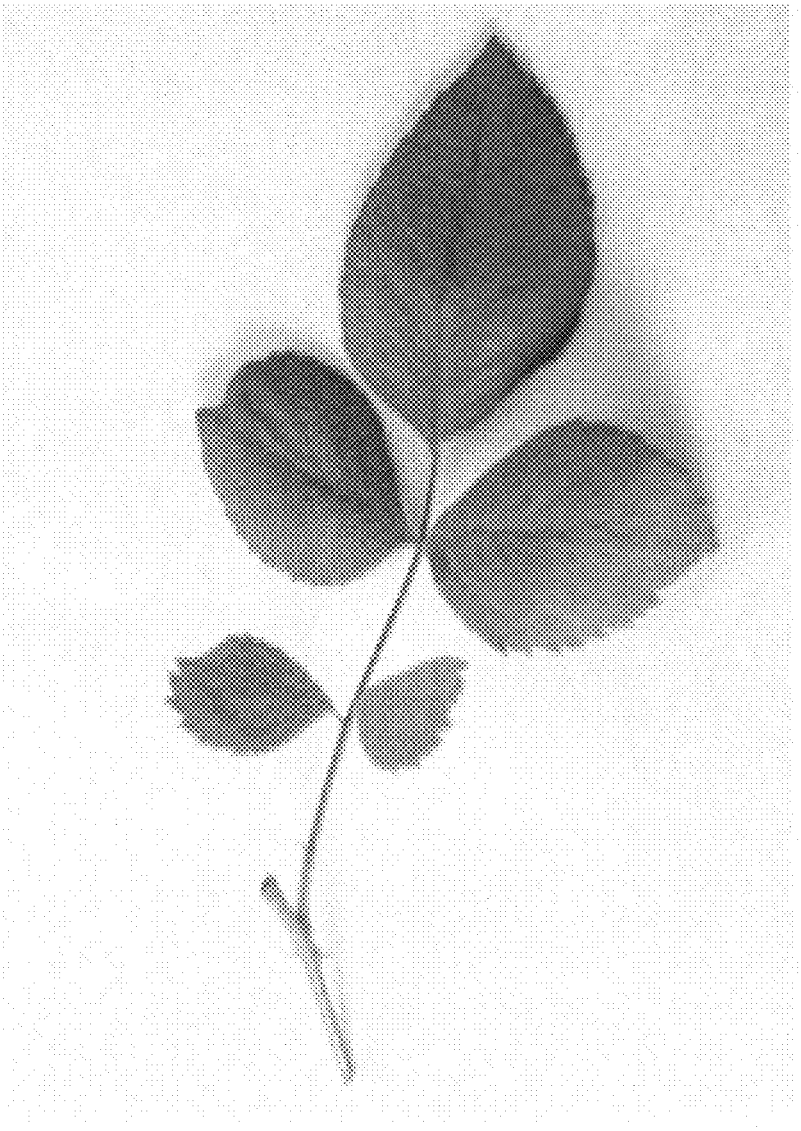
FIG. 3 illustrates foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KASCT491-1' plants grown outdoors in a nursery in Riyadh, Saudi Arabia. The growing temperature ranged from 18° C. to 22° C. at night and 25° C. to 35° C. during the day. No artificial light, photoperiodic treatments or chemical treatments were given to the plants. Plants were note pinched and were grown under shade cloth. Measurements and numerical values represent averages of typical flowering types.

Botanical classification: *Rosa damascena* 'KASCT491-1'.

Commercial classification: Shrub rose.

Age of the plant described: Approximately 1 year from a rooted plantlet.

Container size of the plant described: Growing in the ground.

PROPAGATION

Typical method: Vegetative cuttings.

Time to initiate rooting: Approximately 20 days at 21° C. or higher.

Time to produce a rooted plantlet: Approximately 20 days at 20° C. or higher.

Root description: Fine, fibrous.

PLANT

Height: 90 cm, with an average range between 85 to 95 cm.

Plant spread: 60 cm to 70 cm.

Growth rate: About 8 months to 1 year to reach 90 cm.

Branching characteristics: Densely branched.

Branching characteristics:

Length of primary lateral branches: About 16-18 cms.

Diameter of lateral branches: 0.5 cm.

Quantity of lateral branches: Varies, average 20.

Branching arrangement: Alternate.

Branches-young wood:

*Diameter*.—About 1 cm.

*Texture*.—Glabrous with thorns.

*Approximately density/quantity of thorns*.—Six thorns every 3 cm.

*Color*.—Near RHS Yellow-Green 144C.

Branches-old wood:

*Diameter*.—About 1.5 cm.

*Texture*.—Glabrous with thorns.

*Approximately density/quantity of thorns*.—Six thorns every 3 cms.

*Color*.—Near RHS Yellow-Green 153C.

FOLIAGE

Leaf:

*Arrangement*.—Petiolate, alternate, pinnately compound.

*Quantity*.—About 4-6 per main branch.

*Average length*.—About 10 cm.

*Average width*.—About 6 cm.

Leaflet:

*Quantity*.—Five per leaf.

*Average length*.—3.0-5.0 cm.

*Average width*.—2.0-2.5 cm.

*Shape of blade*.—Oblong.

*Apex*.—Pointed.

*Base*.—Smooth.

*Margin*.—Serrated.

*Texture of top surface*.—Light pubescence.

*Texture of bottom surface*.—Light pubescence.

*Leaf internode length*.—1.5-2.0 cm.

*Color*.—Young foliage upper side: Near RHS Green 141B. Young foliage under side: Near RHS Green 141C. Mature foliage upper side: Near RHS Green 141A. Mature foliage under side: Near RHS Green 141C.

*Venation*.—Type: Reticulate. Venation color upper side: Near RHS Yellow-Green 149A. Venation color under side: Near RHS Yellow-Green 150B.

*Petiole*.—Length: 3 cm. Width: 0.2 cm. Color: Near RHS Yellow-Green 144B. Texture: Smooth. Other characteristics: Stipulate with adnate stipule 1 cm diameter.

FLOWER

Natural flowering season: November to April in Riyadh, Saudi Arabia.

Begins flowering after how many years/months: One month from a rooted plant.

Inflorescence: Terminal raceme.

Rate of flower opening: About 5 to 7 days from bud to fully opened flower.

Flower longevity on plant: 6 days, after fully opened.

Peduncle:

*Length*.—About 0.5 cm.

*Diameter*.—0.2 cm.

Petals:

*Petal arrangement*.—Actinomorphic.

*Size*.—Length: 2.0-3.5 cm. Width: 1.5-3 cm.

*Shape*.—Obovate.

*Margin*.—Smooth.

*Apex*.—Rounded.

*Base*.—Acute.

*Petal quantity*.—42 to 46.

*Texture*.—Soft, somewhat velvety.

Color:

*Petals*.—When opening: Upper surface: Near RHS Red-Purple 68B. Lower surface: Near RHS Red-Purple 73B. Fully opened: Upper surface: Near RHS Red-Purple 68C. Lower surface: Near RHS Red-Purple 73C. Color Changes when aging: Flower becomes lighter in color. Upper surfaces fades to 68D, lower surface to 73D.

Bud:

*Shape*.—Conical.

*Length*.—About 2 cm.

*Diameter*.—About 1.5 cm.

*Color*.—Near RHS Red-Purple 64B.

Sepals:

*Length*.—2.0-2.2 cm.

*Width*.—1.0 cm.

*Shape*.—Lanceolate.

*Color*.—Interior Surface: Near RHS Green 141D. Exterior Surface: Near RHS Green 143A.

*Texture*.—Rough.

Receptacle:

*Length*.—1.0 cm.

*Width*.—0.8 cm.

*Shape*.—Funnel-shaped.

*Color*.—Near RHS Green 142A.

Fragrance: Sweet and strong.

REPRODUCTIVE ORGANS

Stamens:

*Number*.—Numerous.

*Filament length*.—About 0.8-1.0 cm.

*Filament color*.—Near RHS 150D.

Anthers:

*Length*.—0.2 cm.

*Shape*.—Arrowhead.

*Color*.—Near RHS 153C.

*Pollen*.—Numerous.

*Color*.—154D.

*Quantity*.—Numerous.

Pistil:

*Number*.—Numerous, too minute to quantify accurately.

*Length*.—Approximately 0.8 cm.

*Style*.—Length: About 0.5 cm. Color: Near RHS Yellow-Green 154D.

*Stigma*.—Shape: Thickened linear. Color: Near RHS Yellow-Green 154C. Ovary Color: Near RHS Yellow-Green 154D.

OTHER CHARACTERISTICS

Seeds and fruits: No fruit and seed set observed to date.

Disease/pest resistance: The degree of resistance to fungal and insect pests is the same as that of the non-irradiated control.

Temperature tolerance: The variety has been found suitable for climate conditions of the American Horticulture Society heat zone 7.

What is claimed is:

1. A new and distinct *Rosa damascena* plant named 'KASCT491-1' as herein illustrated and described.

* * * * *